(12) United States Patent
Crane

(10) Patent No.: US 7,647,815 B2
(45) Date of Patent: Jan. 19, 2010

(54) METHOD OF IDENTIFYING AND DETECTING THE CONCENTRATIONS OF MULTIPLE SPECIES BY MEANS OF A SPECTROPHONE

(76) Inventor: Robert Anthony Crane, 31 Margaret Ann Avenue, Beaconsfield, Quebec (CA) H9W 5N7

(*) Notice: Subject to any disclaimer, the term of this patent is extended or adjusted under 35 U.S.C. 154(b) by 0 days.

(21) Appl. No.: 11/797,375

(22) Filed: May 3, 2007

(65) Prior Publication Data
US 2007/0256475 A1   Nov. 8, 2007

Related U.S. Application Data

(63) Continuation of application No. 11/086,280, filed on Mar. 23, 2005, now abandoned.

(30) Foreign Application Priority Data
Mar. 24, 2004   (CA) .................................. 2461328

(51) Int. Cl.
G01J 3/433   (2006.01)
(52) U.S. Cl. ................. 73/24.02; 73/24.06; 250/339.06; 250/339.12
(58) Field of Classification Search ................. 73/24.01, 73/24.02, 24.06; 250/339.01, 339.06, 339.12
See application file for complete search history.

(56) References Cited

U.S. PATENT DOCUMENTS

| | | | | |
|---|---|---|---|---|
| 4,055,764 A * | 10/1977 | Dimeff | ..................... | 250/336.1 |
| 4,058,725 A * | 11/1977 | Aine | ........................... | 250/343 |
| 4,457,162 A * | 7/1984 | Rush et al. | .................. | 73/24.01 |
| 4,899,053 A * | 2/1990 | Lai et al. | ..................... | 250/343 |
| 5,834,632 A * | 11/1998 | Olender et al. | ............... | 73/40.7 |
| 5,933,245 A * | 8/1999 | Wood et al. | .................. | 356/437 |
| 5,942,755 A * | 8/1999 | Dreyer | .................. | 250/339.13 |
| 6,089,076 A * | 7/2000 | Mueller et al. | ............. | 73/24.06 |
| 2003/0112019 A1* | 6/2003 | Forster et al. | ................ | 324/633 |

* cited by examiner

Primary Examiner—Daniel S Larkin
(74) Attorney, Agent, or Firm—Steven M. Greenberg, Esq.; Carey, Rodriguez, Greenberg & Paul, LLP

(57) ABSTRACT

A method of identifying and determining the concentrations of multiple species in a gas sample, includes providing a spectrophone assembly having a detector chamber, supplying the gas sample to the detector chamber and simultaneously passing a plurality of radiations of different wavelengths into the detector chamber to produce multiple acoustic resonances of different frequencies. Acoustic resonances in the detector chamber are simultaneously sensed to produce corresponding electrical signals, and the electrical signals are analysed to identify the species present in the gas sample and determine the concentration of each specie.

3 Claims, 5 Drawing Sheets

METHOD OF IDENTIFYING AND DETECTING THE CONCENTRATIONS OF MULTIPLE SPECIES BY MEANS OF A SPECTROPHONE

RELATED APPLICATION

This invention is a continuation of U.S. patent application Ser. No. 11/086,280 filed Mar. 23, 2005, now abandoned.

FIELD OF THE INVENTION

This invention relates to the identification and determination of the concentrations of multiple species in a gas sample by means of a spectrophone.

BACKGROUND OF INVENTION

In laser based photo acoustic spectroscopy, each molecular specie in a detection chamber is basically detected from the response to illumination by laser radiation of a specific wavelength. Absorption of such radiation by a specie in the detector chamber at the specific wavelength produces an amplitude modulated pressure which is detected by a microphone in the detector chamber. Generally, if more than one specie is involved, with interference from unwanted species is to be taken into account, then operation at corresponding different wavelengths is required. The procedure involved ultimately sorts out different species and/or interfering components.

Such a procedure normally requires the operation of a spectrophone at different wavelengths in time sequence, that is to say requires that the laser be tuned in time ordered sequence to different wavelengths. When each wavelength arises from a different and separate source, such as a set of semi conductor lasers each operating at a different wavelength, the illumination from each such laser is injected into the spectrophone in timed sequence. Thus, measurement of multiple species cannot be carried out simultaneously and consequently requires more time for the species to be identified and their concentrations determined.

Further information in this respect can be found in the following references:

Kreuzer, L. B., Journal of Applied Physics, 42, 2934 (1971).
Rosengren, L-G., Infrared Physics, 13, 173 (1973).
Minguzzi, P., Tonelli, M., and Carrozzi, A., Journal of Optical Spectroscopy, 96, 294 (1982).
Morse, P. M., "Vibration and Sound" (McGraw-Hill, New York, 1968).
West, G. A., Barrett, J. J., and Siebert, D. R., Review of Scientific Instruments, 54, 797 (1983).

It is therefore an object of this invention to provide a method simultaneously identifying and determining the concentrations of multiple species by means of a spectrophone.

SUMMARY OF INVENTION

According to the invention, a method of identifying and measuring the concentration of multiple species in a gas sample includes providing a spectrophone assembly having a detector chamber supplying the gas sample to the detector chamber simultaneously passing a plurality of radiations of different wavelengths into the detector chamber to produce multiple acoustic resonances of different frequencies, simultaneously sensing acoustic resonances in the detector chamber and producing corresponding electrical signals, and analyzing said electrical signals to identify the species present in the gas sample and determine the concentration of each specie.

The acoustic resonances may be determined by internal geometry of the detector chamber. The acoustic resonances may be sensed by at least one microphone.

The method may include providing a plurality of detector chambers each with a single or multiple acoustic resonant mode.

The radiation may be modulated amplitude, frequency or phase or by utilizing the Stark effect to modulate the frequency of specie absorption with respect to the frequency or wavelength of the radiation passed into the chamber.

According to one aspect of the invention, a method of identifying and measuring the concentration of multiple species in a gas sample includes providing a spectrophone with a detector chamber which is acoustically resonant at a plurality of different resonant frequencies, simultaneously illuminating the multiple species in the detector chamber with a plurality of lasers each operating at a different wavelength, the radiation from each laser being amplitude modulated at a frequency rate corresponding to a particular resonant frequency, providing microphones in the detector chamber suitably positioned therein and frequency tuned to a corresponding resonant frequency and analyzing signals from the microphones to identify the species present and determine their concentration.

DESCRIPTION OF THE DRAWINGS

Embodiments of the invention will now be described, by way of example, with reference to the accompanying drawings, of which:

FIG. 3b is an end view of the spectrophone chamber of FIG. 3a;

FIG. 4b is an end view of the spectrophone chamber of FIG. 4a;

FIG. 5b is a side view of the spectrophone chamber of FIG. 5a.

DESCRIPTION OF PREFERRED EMBODIMENTS

Figure 1:
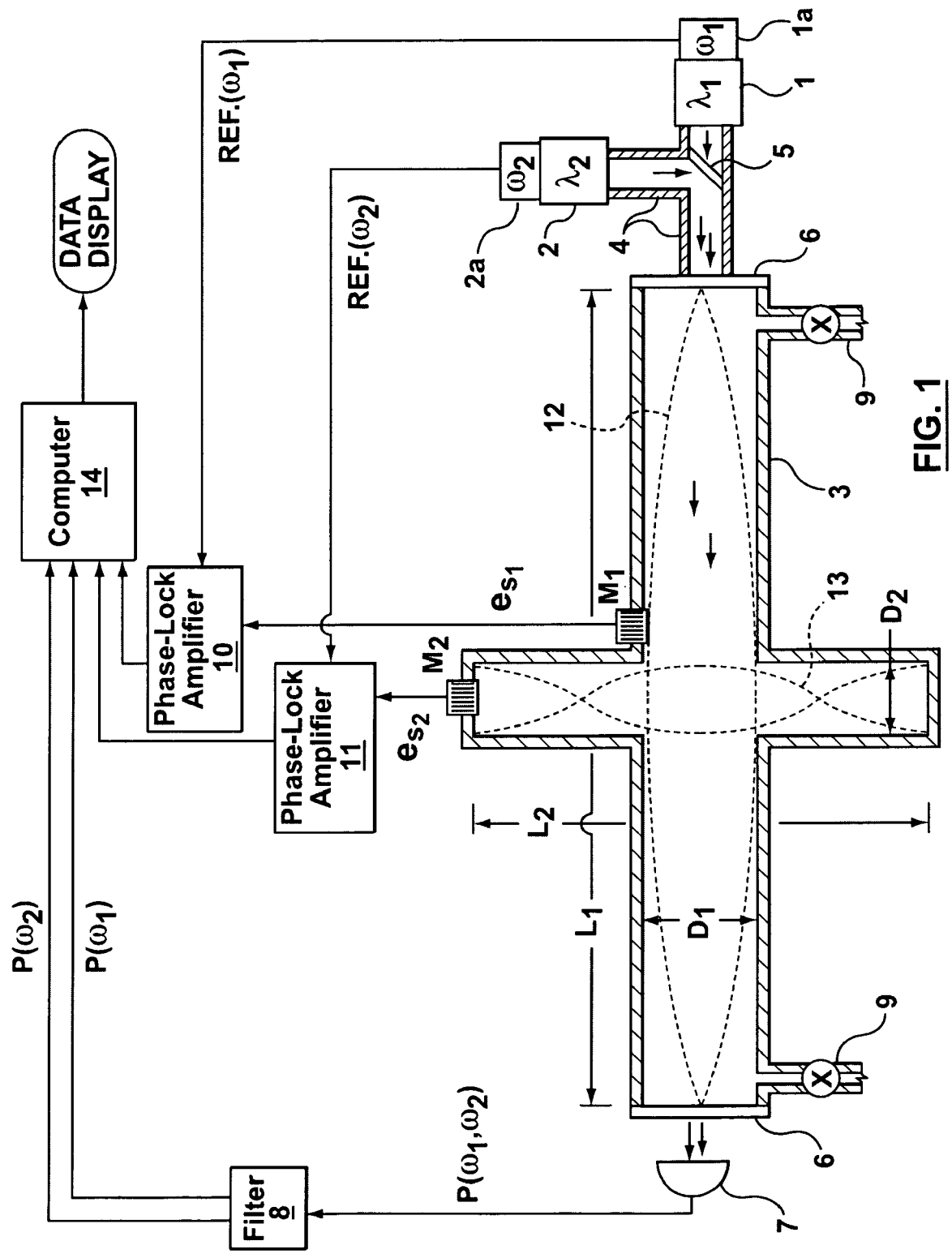
FIG. 1 is a schematic view of a spectrophone assembly in accordance with one embodiment of the invention.

Referring first to FIG. 1 of the drawings, a spectrophone assembly includes a cell or chamber 3 which in use is illuminated by two lasers 1, 2 with different wavelengths $\lambda_1$, $\lambda_2$ respectively. The chamber 3 is formed by two cylindrical tubes with internal length and diameter $L_1$, $D_1$ and $L_2$, $D_2$ respectively, the two tubes being internally connected and vacuum closed to the outside.

The lasers 1, 2 are power modulated at frequencies $\omega_1$ and $\omega_2$ by modulators 1a and 2a respectively and, as references, these frequencies are sent to separate phase-lock amplifiers 10, 11. The laser beams are guided into the chamber 3 by fiber optics or wave guides 4 and the two beams are combined by a dichroic mirror 5 which transmits the beam from laser 1 and reflects the beam from laser 2.

The chamber 3 is closed by two radiation transmitting windows 6 through which the laser beams pass before being received by a radiation power meter 7 adjacent the exit window 6. A single power meter 7 is used to measure the exit powers for both power beams simultaneously. Thus, the power meter 7 must have a response time fast enough to detect beams at both modulation rates $\omega_1$ and $\omega_2$. Alternatively, separate power meters each sensitive to a corresponding modulation rate may be used.

The exit power P measured by power meter 7 is separated by a filter 8 into power components for $\omega_1$ and $\omega_2$ which are then sent to a computer 14 for signal normalization purposes. A gas sample containing trace amounts of the species of interest is passed into and out of the chamber 3 through valved ports 9. The gas sample is typically air at a pressure of about one atmosphere. The sample may be a static gas fill or may be continuously flowed through the chamber 3. The necessary electric power supplies are of course provided as will be readily apparent to a person skilled in the art.

Figure 2:
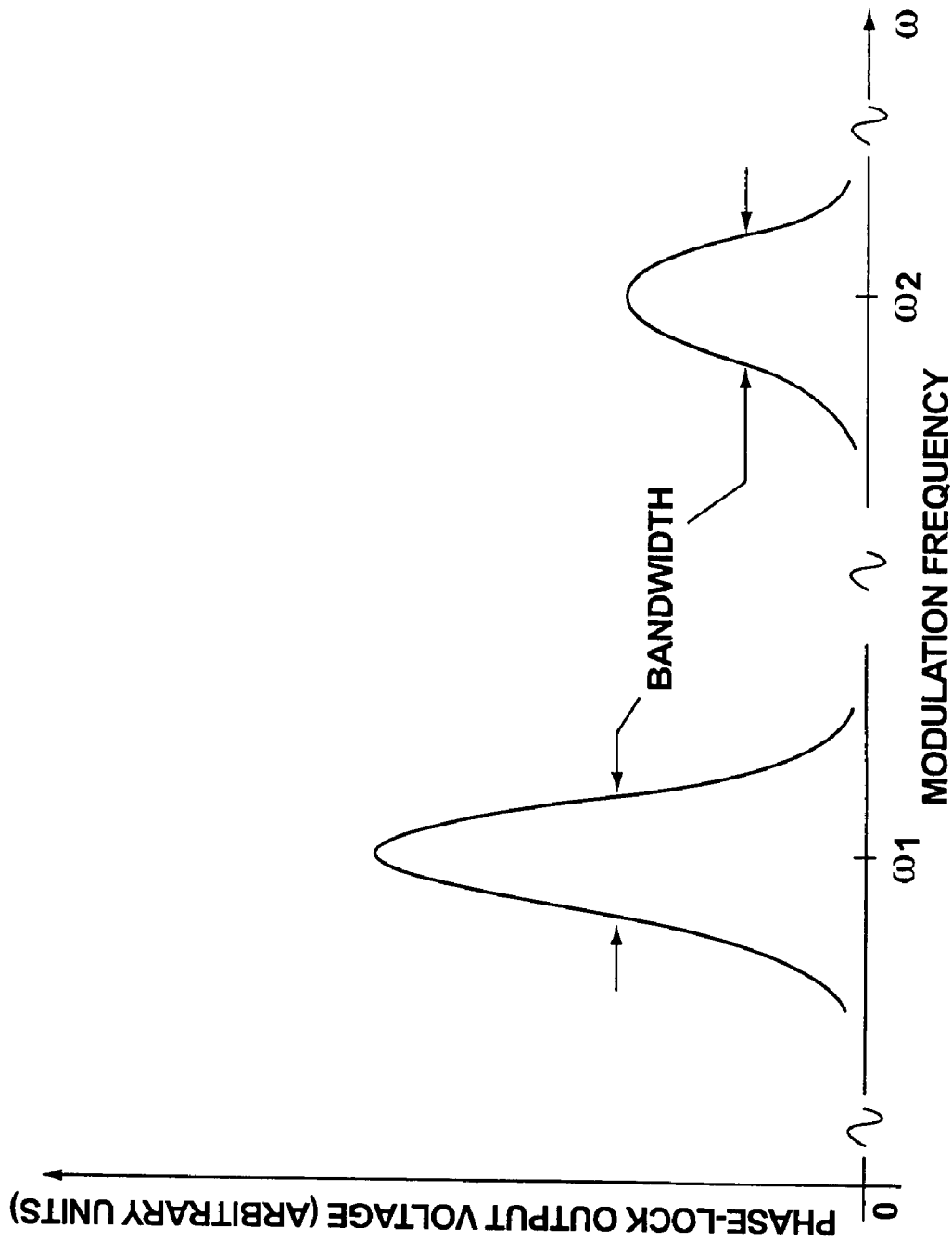
FIG. 2 is a graph showing the separation between modulation frequencies $\omega_1$ and $\omega_2$.

The chamber 3 is provided with microphones $M_1$, $M_2$. The acoustic responses chosen for operation should be sufficiently separated in frequency space such that there will be no overlap in the response from the microphones. This can be effected by proper design and selection of the internal geometry of the chamber 3. FIG. 2 illustrates a typical frequency separation of the two acoustics resonances in this embodiment. Such frequency separation provides a basic filter between the responses of the microphones and also filters substantially all acoustic noise and/or erroneous signals arising from outside the bandwidths of the subject resonances.

Referring now again to FIG. 1, if the specie to be detected has an absorptivity at $\lambda_1$, the absorption will produce gas heating which, because of the fixed chamber volume, causes a pressure change modulated at a frequency of $\omega_1$ which is sensed by internal microphone $M_1$. The resulting electronic signal $e_{s1}$, from microphone $M_1$ is fed to and measured by lock-in amplifier 10. The modulation rate $\omega_1$ corresponds to an acoustic resonance frequency at $\omega_1$ which amplifies the pressure changes at this modulation rate. The frequency bandwidth of the resonance is sufficiently narrow to effectively prevent frequency overlap, within its bandwidth, with other resonances and thereby filters out acoustic signals from any source at frequencies outside the bandwidth of the resonance at $\omega_1$. The resonance frequency is determined by the internal geometry of the chamber 3. Microphone $M_1$ is located at or near a maximum of the pressure standing wave 12, the amplitude of which is shown in FIG. 1.

In a similar manner, microphone $M_2$ is located near a maximum of pressure standing wave 13 in the side arm with length and diameter $L_2$, $D_2$. The resonance in this case is at frequency $\omega_2$ and outside the bandwidth of the resonance at $\omega_1$. The signals $e_{s1}$ and $e_{s2}$ from microphones $M_1$ and $M_2$ respectively are fed for processing to separate phase-locked (lock-in) amplifiers 10, 11, each referenced to the corresponding frequencies $\omega_1$ and $\omega_2$ respectively. The phase-locked amplifiers evaluate the microphone signals, convert them into direct current values and subsequently feed them into the computer 14. The exit powers of the two beams $P(\omega_1)$ and $P(\omega_2)$ required for normalization of the microphone signals are also fed into the computer 14. The computer analyzes the computer data and produces the specie identifications and their concentrations for display.

The acoustic resonances of the chamber 3 are defined by its internal geometry in accordance with the following equation:

$$\omega_{kmn} = \pi c [(k/L)^2 + (\beta_{mn}/R)^2]^{1/2} \quad (1)$$

where $\omega_{kmn}$ is the acoustic resonance frequency, the in radians per second, defined by a cylindrical section of length L between the end boundaries and of internal radius R, c is the velocity of sound for the gas at the pressure and temperature inside the chamber 3, k is an integer having values corresponding to longitudinal harmonics, and $\beta_{mn}$ is the $n^{th}$ root of the derivative of the Bessel function $J_m(\pi\beta)$, of order m, with respect to $\beta$.

It should be noted that the acoustic resonance is a pressure standing wave where the boundaries defining the length L can be any discontinuity in the cross section, such as the window boundary at each end of the chamber 3. The windows need not even be present, i.e. the ends of the cell may be open. The basic fact is that these boundaries define the standing wave nodes of zero pressure. Each tubular section of the cell (as shown being utilized by microphones $M_1$ and $M_2$) has available to it a number of resonances defined by the values of k, m and n and the sum and difference resonance frequencies by various combinations of resonances arising from the two sections shown in FIG. 1. All of the differing resonances can be used to increase the number of radiation sources of different wavelengths illuminating the chamber 3 where each source is modulated and its microphone response is processed at its resonance frequency.

There are many internal geometrical configurations of the chamber 3 which promote acoustic resonances. To illustrate the principles involved, FIGS. 3a, 3b, 4a, 4b, 5a and 5b show schematics of some configurations (with the pressure profile indicated by dotted lines) for some resonant pressure standing waves. The maxima are the most desirable locations for a microphone.

Figure 3A:
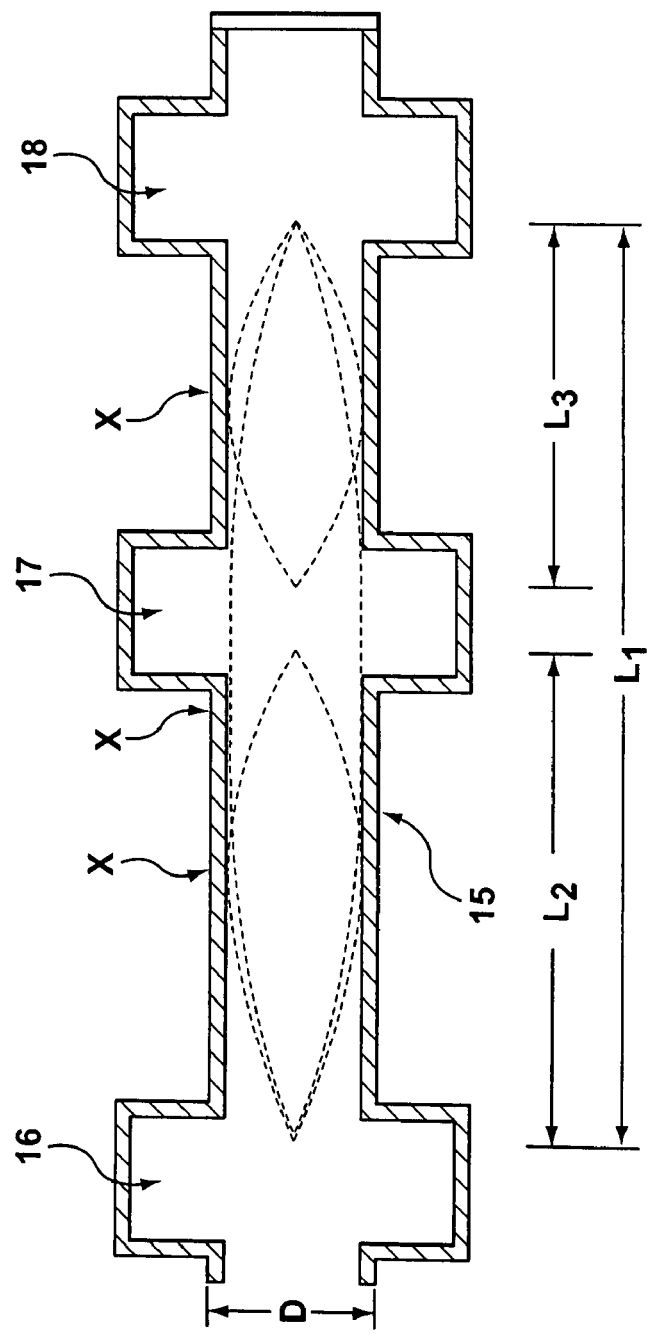
FIG. 3a is a side view of a spectrophone in accordance with another embodiment of the invention.
Figure 3B:
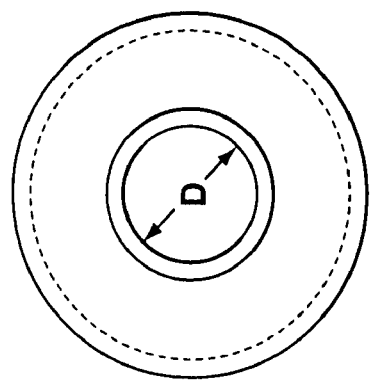

FIGS. 3a and 3b show fundamental resonance modes available with the geometry illustrated. The expansion bulbs 16, 17, 18 define the lengths to determine the resonance frequency by equation (1) for each case. The expansion bulbs 16, 17, 18 provide an abrupt change in the tube cross section which is sufficient to force a pressure node (zero pressure point) within the vicinity of the entrance to the bulb. The chamber 15 need not be closed at both ends. As shown, one end is open. FIG. 3 shows the best locations X for a microphone for each resonance. A single microphone of sufficient frequency bandwidth can be located in an overlapping region of two or more resonances where the pressure value in each case is non-zero.

Figure 4B:
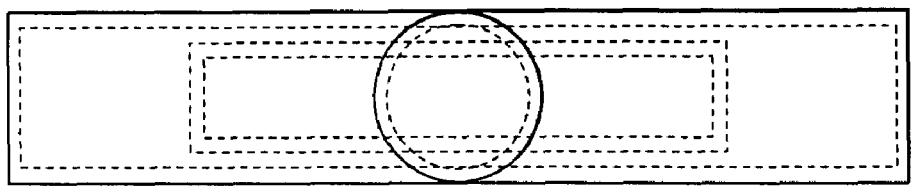
Figure 4A:
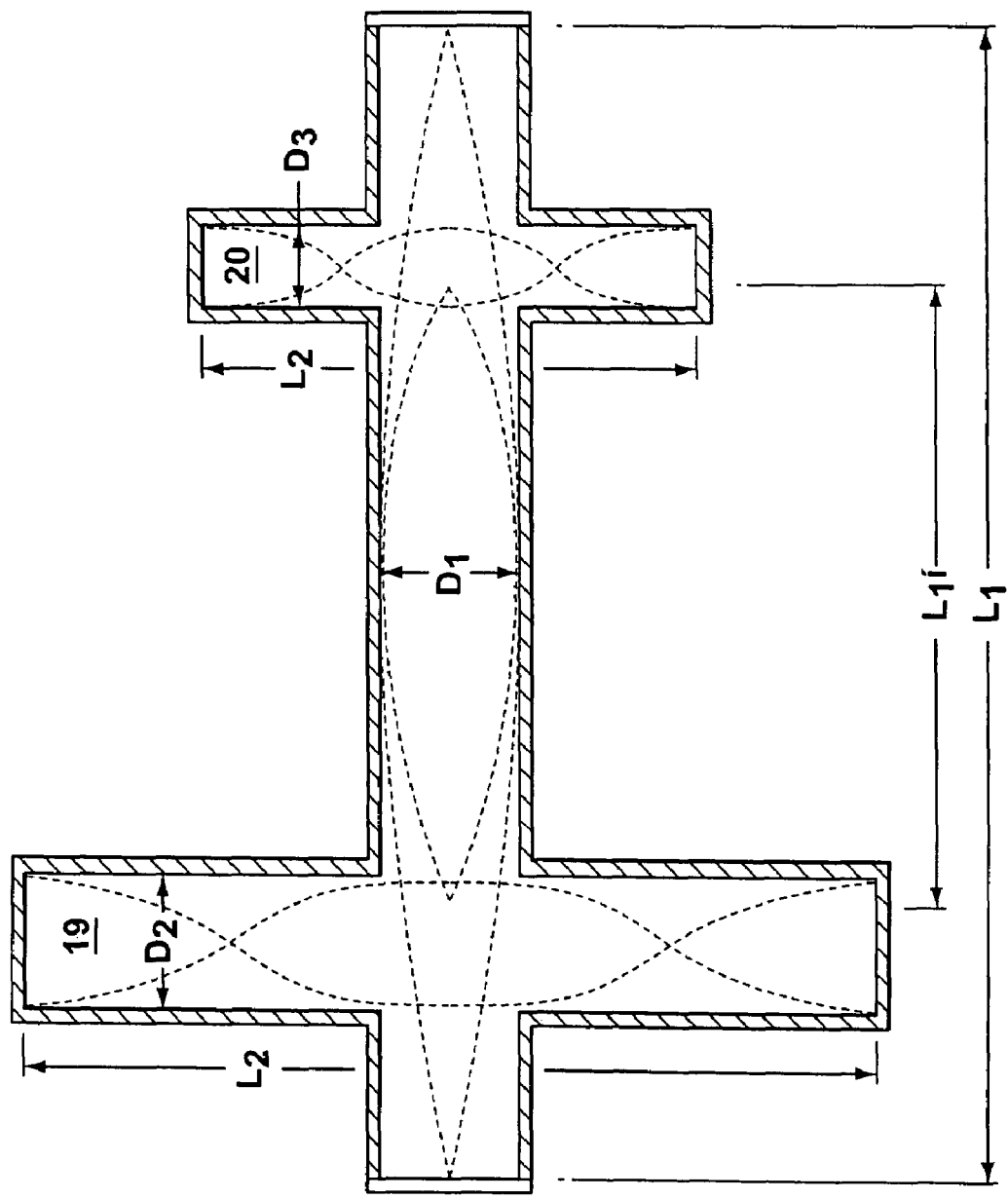
FIG. 4a is a side view of a spectrophone chamber in accordance with a still further embodiment of the invention.

FIGS. 4a and 4b show a configuration with two resonance side arms 19, 20 to provide difference resonance frequencies, the side arms 19, 20 having non-equal length and/or diameters as illustrated. Various other resonances, all of different frequencies, can of course be obtained from the geometry shown.

Figure 5B:
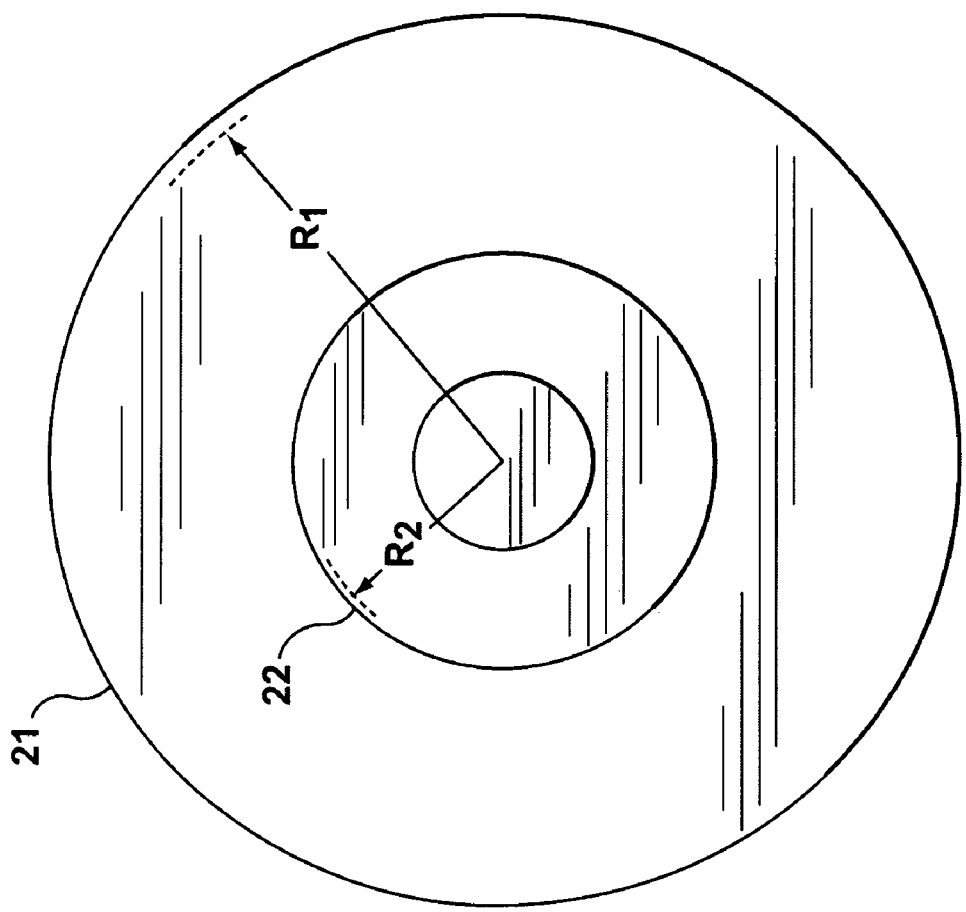
Figure 5A:
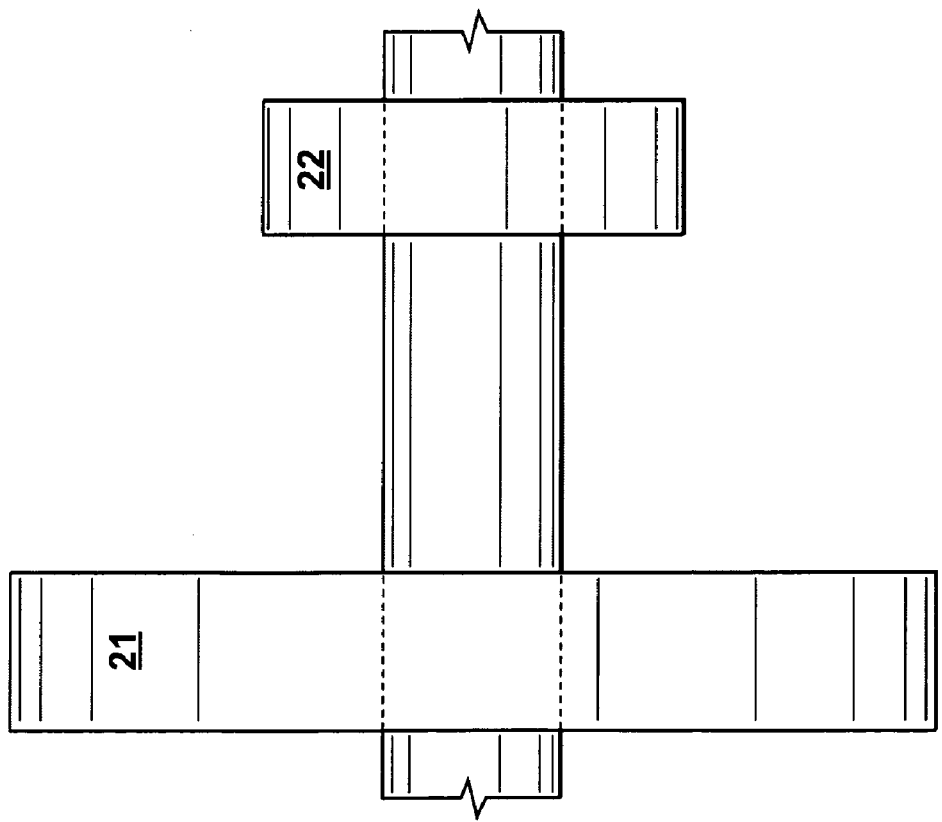
FIG. 5a is a side view of a spectrophone chamber in accordance with yet another embodiment of the invention.

FIGS. 5a and 4b show a configuration similar to that of FIG. 4 except that the side arm tubes 19, 20 are replaced by the geometries of disks 21, 22 of radii $R_1$, $R_2$ respectively. The acoustic resonances in these disks will be dominated by the second term ($\pi c \beta_{min}/R$), i.e. the radial patterns of standing pressure waves, of equation (1). Additional resonance frequencies are also obtainable from harmonics or overtones and combinations in terms of sums and difference frequencies of these fundamental resonances. Further, the same principles apply to rectangular cross sections or any geometry where there will be points between which pressure standing waves can be produced.

Thus, as described above, a photo acoustic cell can be simultaneously illuminated by a number of radiation sources, each of different wavelength, and simultaneously analyzing a gas sample in the cell for its specie identifications and concentrations. The gas pressure in the chamber may be in the range of from about 0.1 TORR to as high as practically possible, and the detectable concentration of a specie may range from a trace to 100%.

The advantages and other embodiments of the invention will now be readily apparent to a person skilled in the art, the scope of the invention being defined in the appended claims.

What is claimed is:

1. A method of identifying and determining the concentrations of multiple species in a gas sample, the method comprising:

providing a spectrophone assembly having a single detector chamber;

supplying the gas sample to the detector chamber;

simultaneously passing a plurality of radiations each of a different wavelength into the single detector chamber to simultaneously produce multiple acoustic resonances of different frequencies, said acoustic resonances being pressure standing waves defined by internal geometry of the detector chamber;

simultaneously sensing said acoustic resonances in the detector chamber and producing corresponding electrical signals; and analyzing said electrical signals to identify the species present in the gas sample and determine the concentration of each specie.

2. A method according to claim 1 wherein the acoustic resonances are sensed by at least one microphone.

3. A method according to claim 1 wherein the radiation is modulated in amplitude, frequency or phase or by utilizing the Stark effect to modulate the frequency of specie absorption with respect to the frequency or wavelength of the radiation passed into the chamber.

* * * * *